US012778425B2

(12) United States Patent
Zhu et al.

(10) Patent No.: US 12,778,425 B2
(45) Date of Patent: Nov. 3, 2026

(54) METHOD AND DEVICE FOR CALCULATING IPA OF INTRALUMINAL OCT IMAGE

(71) Applicant: SHENZHEN VIVOLIGHT MEDICAL DEVICE & TECHNOLOGY CO., LTD., Shenzhen (CN)

(72) Inventors: Rui Zhu, Shenzhen (CN); Quanmao Lu, Shenzhen (CN); Chao Liu, Shenzhen (CN); Peng Bi, Shenzhen (CN)

(73) Assignee: SHENZHEN VIVOLIGHT MEDICAL DEVICE & TECHNOLOGY CO., LTD., Shenzhen (CN)

( * ) Notice: Subject to any disclaimer, the term of this patent is extended or adjusted under 35 U.S.C. 154(b) by 156 days.

(21) Appl. No.: 18/287,016

(22) PCT Filed: Aug. 13, 2021

(86) PCT No.: PCT/CN2021/112620
§ 371 (c)(1),
(2) Date: Aug. 22, 2024

(87) PCT Pub. No.: WO2023/284055
PCT Pub. Date: Jan. 19, 2023

(65) Prior Publication Data
US 2025/0325184 A1 Oct. 23, 2025

(30) Foreign Application Priority Data
Jul. 13, 2021 (CN) ........................ 202110790327.3

(51) Int. Cl.
*A61B 5/00* (2006.01)
*A61B 5/02* (2006.01)
(Continued)

(52) U.S. Cl.
CPC .......... *A61B 5/0066* (2013.01); *A61B 5/0084* (2013.01); *A61B 5/02007* (2013.01);
(Continued)

(58) Field of Classification Search
CPC A61B 5/0066; A61B 5/7267; G06V 10/7715; G06T 2207/20084
See application file for complete search history.

(56) References Cited

U.S. PATENT DOCUMENTS

2005/0249391 A1 11/2005 Kimmel et al.
2017/0309018 A1 10/2017 Shalev et al.
(Continued)

FOREIGN PATENT DOCUMENTS

CN 105096270 A 11/2015
CN 106061387 A 10/2016
(Continued)

OTHER PUBLICATIONS

CN Office Action dated Aug. 9, 2024 for in application No. 202110790327.3.
(Continued)

*Primary Examiner* — Anne M Kozak
*Assistant Examiner* — Kaitlyn Eunji Kim
(74) *Attorney, Agent, or Firm* — Maschoff Brennan

(57) ABSTRACT

A method for calculating an IPA of an intravascular OCT image, relating to the technical field of medical instruments, the method including: acquiring an intravascular OCT image (S101); determining a calcified plaque region of the intravascular OCT image (S102); determining a light attenuation coefficient of the intravascular OCT image, where the light attenuation coefficient of the intravascular OCT image does not include a light attenuation coefficient of the calcified plaque region (S103); and determining an IPA of the intravascular OCT image according to the light attenuation
(Continued)

coefficient of the intravascular OCT image (S104). The above method can increase accuracy of an IPA.

8 Claims, 4 Drawing Sheets

(51) Int. Cl.
*G06T 7/00* (2017.01)
*G06V 10/25* (2022.01)
*G06V 10/77* (2022.01)
*G06V 10/774* (2022.01)
*G06V 10/776* (2022.01)
*G06V 10/82* (2022.01)

(52) U.S. Cl.
CPC .......... *A61B 5/7246* (2013.01); *A61B 5/7267* (2013.01); *A61B 5/7485* (2013.01); *G06T 7/0012* (2013.01); *G06V 10/25* (2022.01); *G06V 10/7715* (2022.01); *G06V 10/774* (2022.01); *G06V 10/776* (2022.01); *G06V 10/82* (2022.01); *A61B 2562/0238* (2013.01); *A61B 2576/02* (2013.01); *G06T 2207/10101* (2013.01); *G06T 2207/20081* (2013.01); *G06T 2207/20084* (2013.01); *G06T 2207/30101* (2013.01); *G06V 2201/03* (2022.01)

(56) References Cited

U.S. PATENT DOCUMENTS

2020/0222018 A1* 7/2020 van Walsum ........ A61B 5/0044
2020/0226422 A1* 7/2020 Li et al. ................... G06K 9/62
2021/0192717 A1* 6/2021 Sadoughi et al.

FOREIGN PATENT DOCUMENTS

CN 107993221 A 5/2018
CN 108961229 A 12/2018
CN 112927212 A * 3/2021 ............... G06T 7/00

OTHER PUBLICATIONS

Cheng Kang-lin et al.,"Detection of multislice computed tomography angiography on vulnerable coronary artery plaques," South China Journal of Cardiovascular Diseases, Sep. 2013, vol. 19, No. 5.

* cited by examiner (a) OCT image (b) Calcified region of interest image (a) Result of identifying calcification using a deep learning model (b) Result of identifying calcification using this technical solution

METHOD AND DEVICE FOR CALCULATING IPA OF INTRALUMINAL OCT IMAGE

This application claims priority to Chinese patent application No. 202110790327.3, entitled "METHOD AND DEVICE FOR CALCULATING IPA OF INTRAVASCULAR OCT IMAGE", filed with the China National Intellectual Property Administration on Jul. 13, 2021, the disclosure of which is hereby incorporated by reference in its entirety.

TECHNICAL FIELD

This application relates to the technical field of medical instruments, and in particular, to a method and device for calculating an IPA of an intravascular OCT image.

BACKGROUND

Optical coherence tomography (OCT) has high resolution, and already becomes a commonly used imaging technique in percutaneous coronary intervention (PCI) surgery. In an intravascular OCT image, different intravascular tissue has different light attenuation coefficients. Therefore, different intravascular tissue may be distinguished by using light attenuation coefficients.

TCFA, as a vulnerable plaque, is closely related to the occurrence of cardiovascular diseases, and is the main cause of diseases such as thrombus, acute coronary syndrome, and coronary heart disease. Therefore, the accurate identification of the presence and severity of TCFA in cardiovascular is of great significance in prevention and diagnosis of cardiovascular diseases. An index of plaque attenuation (IPA) is an identification indicator calculated based on a light attenuation coefficient, and can adequately distinguish between thin-cap fibroatheroma (TCFA) (that is, an unstable plaque) and fibroatheroma (FA) (that is, a stable plaque). For example, the IPA is used to identify whether intravascular blood vessel tissue contains TCFA. When intravascular blood vessels contain TCFA, the calculation result of the IPA is higher than the given threshold, and it may be determined that the intravascular blood vessels contain TCFA. When intravascular blood vessels do not contain TCFA, the calculation result of IPA is lower than the given threshold, and it may be determined that the intravascular blood vessels do not contain TCFA. However, when intravascular blood vessel tissue contains a calcified plaque, the calculation result of the IPA is still higher than the given threshold. In this case, the calculation result of the IPA cannot accurately reflect whether the intravascular blood vessels contain TCFA.

Technical Issues

A technical problem to be resolved in this application is how to improve IPA accuracy.

Technical Solutions

This application provides a method for calculating an IPA of an intravascular OCT image, which may improve IPA accuracy.

According to a first aspect, a method for calculating an IPA of an intravascular OCT image is provided, including: acquiring an intravascular OCT image; determining a calcified plaque region of the intravascular OCT image; determining a light attenuation coefficient of the intravascular OCT image, where the light attenuation coefficient of the intravascular OCT image does not include a light attenuation coefficient of the calcified plaque region; and determining an IPA of the intravascular OCT image according to the light attenuation coefficient of the intravascular OCT image.

The above method may be performed by a terminal device or a chip in a terminal device. intravascular blood vessel tissue is used as an example. When calcification occurs in blood vessels, a blood vessel OCT image obtained by capturing calcified blood vessels by an OCT device contains a calcified plaque region. If the calcified plaque region in the blood vessel OCT image is not removed, an IPA value corresponding to a light attenuation coefficient image corresponding to the blood vessel OCT image is directly calculated, and the calculation result of the IPA will be high. However, in this case, it cannot be determined, according to the calculation result of the IPA, that TCFA is definitely present in the blood vessel OCT image. The reason lies in that regardless of whether TCFA is present in the blood vessel OCT image, provided that the calcified plaque region is present in the blood vessel OCT image, due to the calcified plaque region, a light attenuation coefficient of the calcified plaque region in the light attenuation coefficient image corresponding to the blood vessel OCT image is increased, resulting in a high IPA value calculated based on the light attenuation coefficient. If the calcified plaque region in the blood vessel OCT image is removed, for example, the light attenuation coefficient corresponding to the calcified plaque region in the blood vessel OCT image is set to 0, and then the IPA value of the light attenuation coefficient image after the calcified plaque region is removed is calculated. If a calculation result of the IPA value is greater than a pre-set value, it may be determined that TCFA is present in the blood vessel OCT image. If the calculation result of the IPA value of the light attenuation coefficient image is less than the pre-set value, it may be determined that TCFA is not present in the blood vessel OCT image. As can be seen, the IPA value of the light attenuation coefficient image corresponding to the blood vessel OCT image may be accurately calculated only after the calcified plaque region in the blood vessel OCT image is removed, and it can be determined, according to the IPA value, whether TCFA is present in the blood vessel OCT image.

Optionally, the step of determining a calcified plaque region of the intravascular OCT image includes: processing the intravascular OCT image by using a target convolutional neural network to determine the calcified plaque region of the intravascular OCT image. Compared with that medical specialists annotate calcified plaque regions of intravascular OCT images by using professional software, this application uses a method for identifying a calcified plaque region of an intravascular OCT image with a target neural network, so that a calcified plaque region may be quickly and accurately identified.

Optionally, the target convolutional neural network is obtained through training by using the following method: processing an intravascular OCT training image by using a convolutional neural network to be trained to generate the first feature map; acquiring a texture feature matrix of a calcified plaque region in the intravascular OCT training image; generating a predicted mask according to the first feature map and the texture feature matrix; acquiring a region of interest of the intravascular OCT training image, where the region of interest is used for representing a calcified plaque region in the intravascular OCT training image; and training the convolutional neural network to be trained according to the predicted mask, the region of interest, and a standard mask to generate the target convolutional neural network, where the predicted mask is a predicted value, the standard mask is an actual value, and the region of interest is used for improving a learning capability of a loss function of the convolutional neural network to be trained for edge structure information of the calcified plaque region.

The first feature map generated by processing the intravascular OCT training image by using the convolutional neural network to be trained and the texture feature matrix of the calcified plaque region in the intravascular OCT training image are spliced to generate the predicted mask. The convolutional neural network to be trained is trained by using the predicted mask in combination with the region of interest and the standard mask, to generate the target convolutional neural network. The region of interest is used for improving a learning capability of a loss function of the convolutional neural network to be trained for edge structure information of the calcified plaque region. In addition, the identification precision of the edge structure information of the calcified plaque region is increased by increasing a weight of the region of interest in the loss function. When the calcified plaque region in the intravascular OCT image is identified by using only a deep learning model, identification precision of an irregular edge of the calcified plaque region is low. Therefore, this application provides using a region of interest and a texture feature of an intravascular OCT image to assist in training the convolutional neural network to be trained, to enable the target neural network to accurately identify the calcified plaque region in the intravascular OCT image.

Optionally, the step of acquiring a region of interest of the intravascular OCT training image includes: acquiring a plurality of A-lines of the intravascular OCT training image; and determining the region of interest of the intravascular OCT training image according to the pixel corresponding to the largest light attenuation coefficient on each A-line in the plurality of A-lines.

Optionally, the step of generating a predicted mask according to the first feature map and the texture feature matrix includes: splicing the first feature map and the texture feature matrix to generate a second feature map; and performing dimensionality reduction on the second feature map to generate the predicted mask.

Optionally, the step of performing dimensionality reduction on the second feature map includes: performing the dimensionality reduction on the second feature map by using three 1×1 convolutional layers.

Optionally, the step of acquiring a texture feature matrix of a calcified plaque region in the intravascular OCT training image includes: determining a spatial gray-level co-occurrence matrix of the intravascular OCT training image; determining at least one texture feature of the intravascular OCT training image according to the spatial gray-level co-occurrence matrix; and determining the texture feature matrix according to the texture feature.

Optionally, the at least one texture feature includes: one or more of energy, inertia, entropy, and correlation.

According to a second aspect, a device for calculating an IPA of an intravascular OCT image is provided. The device includes a processor and a memory, the memory is configured to store a computer program, and the processor is configured to call the computer program from the memory and run the computer program, to enable the device to implement the method in the first aspect.

According to a third aspect, a non-transient computer-readable storage medium is provided. The non-transient computer-readable storage medium stores a computer program, and the computer program, when executed by a processor, enables the processor to implement the method in the first aspect.

BRIEF DESCRIPTION OF DRAWINGS

To describe the technical solutions in the embodiments of this application more clearly, the following briefly introduces the accompanying drawings required for describing the embodiments or exemplary technologies. Apparently, the accompanying drawings in the following description show merely some embodiments of this application, and a person of ordinary skill in the art may still derive other drawings from these accompanying drawings without creative efforts.

DETAILED DESCRIPTION

Figure 1:
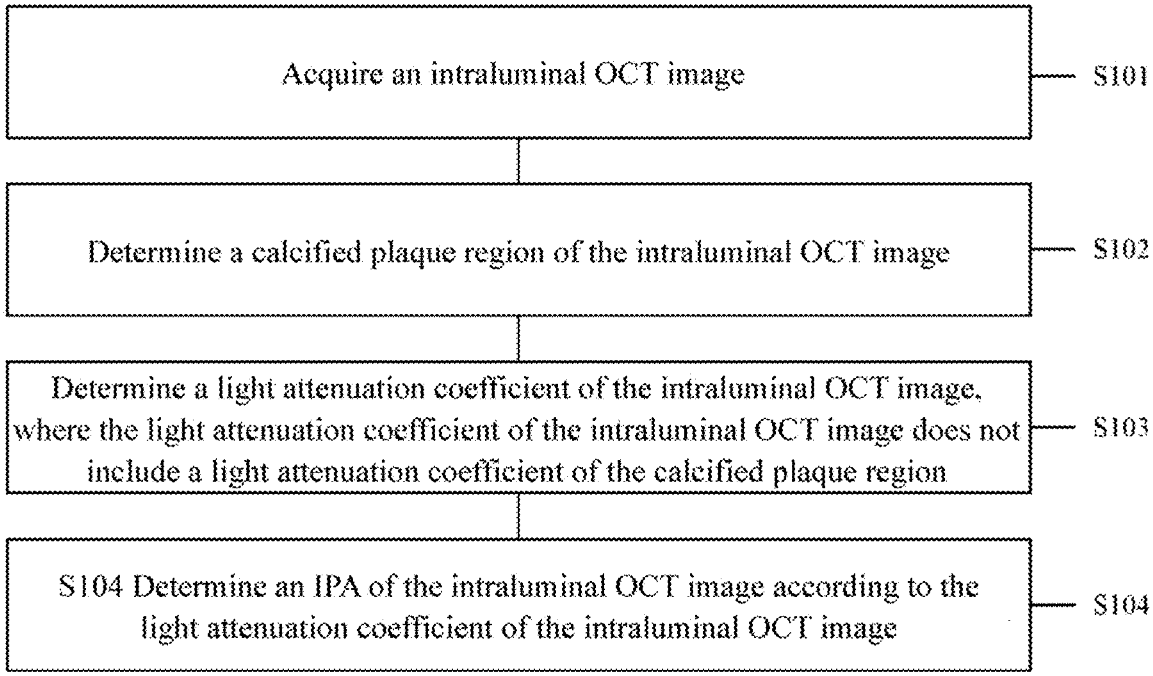
FIG. 1 is a schematic flowchart of a method for calculating an IPA of an intravascular OCT image according to an embodiment of the present application.

To make the objectives, technical solutions, and advantages of this application more comprehensible, this application is further described below in detail with reference to the accompanying drawings and embodiments. It should be understood that the specific embodiments described herein are merely used to describe this application rather than limiting this application.

It needs to be noted that when a component is "fastened to" or "disposed in" another component, it may be directly on the another component or indirectly on the another component. When a component is "connected" to another component, it may be connected directly or indirectly to the another component. The orientations or positional relationships indicated by the terms "up", "down", "left", "right", and the like are orientations or positional relationships based on the accompanying drawings, are merely for the ease of description, are not intended to indicate or imply that the apparatus or component must have a particular orientation or must be constructed and operated in a particular orientation, and therefore are not to be construed as a limitation of this application. A person of ordinary skill in the art may understand the specific meanings of the foregoing terms in accordance with the specific circumstances. The terms "first" and "second" are used only for ease of description, but are not intended to indicate or imply relative importance or implicitly specify a quantity of indicated technical features. The term "plurality of" means two or more, unless specifically and specifically limited otherwise.

This application is further described below in detail with reference to the accompanying drawings and specific embodiments.

In an intravascular OCT image, different intravascular tissues have different light attenuation coefficients. Therefore, different intravascular tissues may be distinguished by using light attenuation coefficients. An IPA is an identification indicator calculated based on a light attenuation coefficient, and may adequately distinguish between TCFA (that is, an unstable plaque) and FA (that is, a stable plaque). For example, the IPA is used to identify whether intravascular blood vessel tissue contains TCFA. When intravascular blood vessels contain TCFA, a calculation result of the IPA will be high (greater than a given threshold), and it may be determined that the intravascular blood vessels contain TCFA. When intravascular blood vessels do not contain TCFA, a calculation result of IPA will be low (less the than given threshold), and it may be determined that the intravascular blood vessels do not contain TCFA. However, when intravascular blood vessel tissue contains a calcified plaque, the calculation result of the IPA is slightly higher (greater than the given threshold). In this case, the calculation result of the IPA cannot accurately reflect whether the intravascular blood vessels contain TCFA. Therefore, how to improve IPA accuracy is currently an urgent problem to be resolved.

This application provides a method for calculating an IPA of an intravascular OCT image, which may improve IPA accuracy. As shown in FIG. 1, the method includes the following steps.

S101: Acquire an intravascular OCT image.

For example, intravascular blood vessel tissue is used as an example. A blood vessel OCT image may be acquired by using an OCT device. Specifically, the OCT device is operated to obtain blood vessel OCT images, then a set of OCT pullback data is obtained. The set of OCT pullback data contains 300 temporally adjacent blood vessel OCT images. For example, for calcified blood vessel (that is, a blood vessel in which calcification occurs), the OCT device is operated to obtain blood vessel OCT images, then a set of calcified data is obtained. The set of calcified data contains 300 blood vessel OCT images. If at least 50 sets of the above calcified data is collected to construct a training dataset, the training dataset at least includes 15000 (that is, 50×300) blood vessel OCT training images. Each blood vessel OCT training image includes a calcified plaque region.

S102: Determine a calcified plaque region of the intravascular OCT image.

For example, intravascular blood vessel tissue is used as example. A training dataset that is constructed from 50 sets of the above calcified data (that is, contains 15000 blood vessel OCT training images) is used as an example. A number of medical specialists, for example, 30 medical specialists, from several centers are invited to manually annotate calcified plaque regions of 15000 blood vessel OCT training images separately by using professional software (for example, Labelme software). A specific annotation method is as follows: If an A location range of a blood vessel OCT training image is annotated by more than half of the medical specialists together as a calcified plaque region, it is considered that the A location range of the blood vessel OCT training image is a calcified plaque region, so that the calcified plaque region of the blood vessel OCT training image annotated by the medical specialists is used as a gold standard for the calcified plaque region of the blood vessel OCT training image. Each blood vessel OCT training image in the training dataset is annotated in this manner. Finally, the gold standard (that is, a standard mask) for the calcified plaque region of the training dataset is obtained.

For example, after calcification occurs in a blood vessel, an imaging characteristic of a calcified plaque in the blood vessel OCT image is manifested as a sharp boundary of a calcified plaque region, a nonuniform distribution of a calcified plaque region, and a dark region in which a calcified plaque region is irregularly distributed. If the calcified plaque region in the blood vessel OCT image is identified by using only a deep learning model, it is very difficult to implement accurate identification of an irregular edge of a calcified plaque region. In addition, in the blood vessel OCT image, there is a certain difference between imaging characteristics of deep calcification and superficial calcification, which tends to cause incorrect detection during detection of an edge of a calcified plaque region by using a deep learning model. Therefore, this application provides a technical solution of using texture features of a region of interest (that is, a calcified region of interest image) and a blood vessel OCT training image to assist in training of a convolutional neural network to be trained to generate a target convolutional neural network and then identifying the calcified plaque region in the blood vessel OCT image by using the target convolutional neural network.

First, calculation of a region of interest (that is, a calcified region of interest image) using a light attenuation model is described.

For example, the step of acquiring a region of interest of the intravascular OCT training image includes: acquiring a plurality of A-lines of the intravascular OCT training image; and determining the region of interest of the intravascular OCT training image according to the pixel corresponding to the largest light attenuation coefficient on each A-line in the plurality of A-lines.

Intravascular blood vessel tissue is used as an example. A blood vessel OCT image (that is, a blood vessel OCT training image) acquired by the OCT device is a blood vessel OCT image in a polar coordinate system. Therefore, a light attenuation coefficient of a single pixel of each blood vessel OCT training image may be calculated by using a light attenuation model in the polar coordinate system. A value of the light attenuation coefficient corresponding to each pixel is used to replace a value of each pixel in the blood vessel OCT training image, to obtain a single light attenuation coefficient training image corresponding to a single blood vessel OCT training image in the polar coordinate system. A calculation formula of the above light attenuation model is as follows:

$$<I_d(r)> = I_0 T(r)\hat{S}(r)\exp(-\mu_t r) \quad (1)$$

$$T(r) = \left[\left(\frac{r-z_0}{z_R}\right)^2 + 1\right]^{-\frac{1}{2}} \quad (2)$$

$$\hat{S}(r) = \begin{cases} 1, & \text{time domain } OCT \\ \exp\left[-\left(\frac{r-z_C}{z_W}\right)^2\right], & \text{swept-source } OCT \end{cases} \quad (3)$$

wherein, $I_0$ is a scale factor, r represents an image depth, T(r) is a vertical point spread function. $Z_0$, $Z_R$, $Z_C$, and $Z_W$ respectively represent a light waist location, a Rayleigh length, a scan center, and a half-width of a roll-off function, and have values of 0, 3 mm, 0, and 10 um, respectively. $u_t$ is the light attenuation coefficient (that is, a to-be-solved variable). A logarithmic operation is performed on both sides of Formula (1), and then the light attenuation coefficient $u_t$ may be calculated by using a least squares method.

A single blood vessel OCT image (that is, blood vessel OCT training image) acquired by the OCT device is used as an example to describe how to obtain a corresponding single light attenuation coefficient training image from a single blood vessel OCT training image. Because the single blood vessel OCT training image acquired by the OCT device is 642×500. 500 refers to that a total of 500 A-lines are obtained when a catheter performs a 360° pullback in a blood vessel, and 642 refers to that 642 pixels are obtained on each A-line. A light attenuation coefficient of each pixel of the single blood vessel OCT training image is calculated by using the light attenuation model to obtain a single light attenuation coefficient training image corresponding to the blood vessel OCT training image. The single light attenuation coefficient training image is also 642×500. 500 refers to that a total of 500 A-lines are obtained when a catheter performs a 360° pullback in a blood vessel, and 642 refers to that 642 pixels are obtained on each A-line (that is, a light attenuation coefficient value corresponding to each pixel in the single blood vessel OCT training image, that is, 642 refers to that 642 light attenuation coefficient values are obtained on each A-line).

Figure 2:
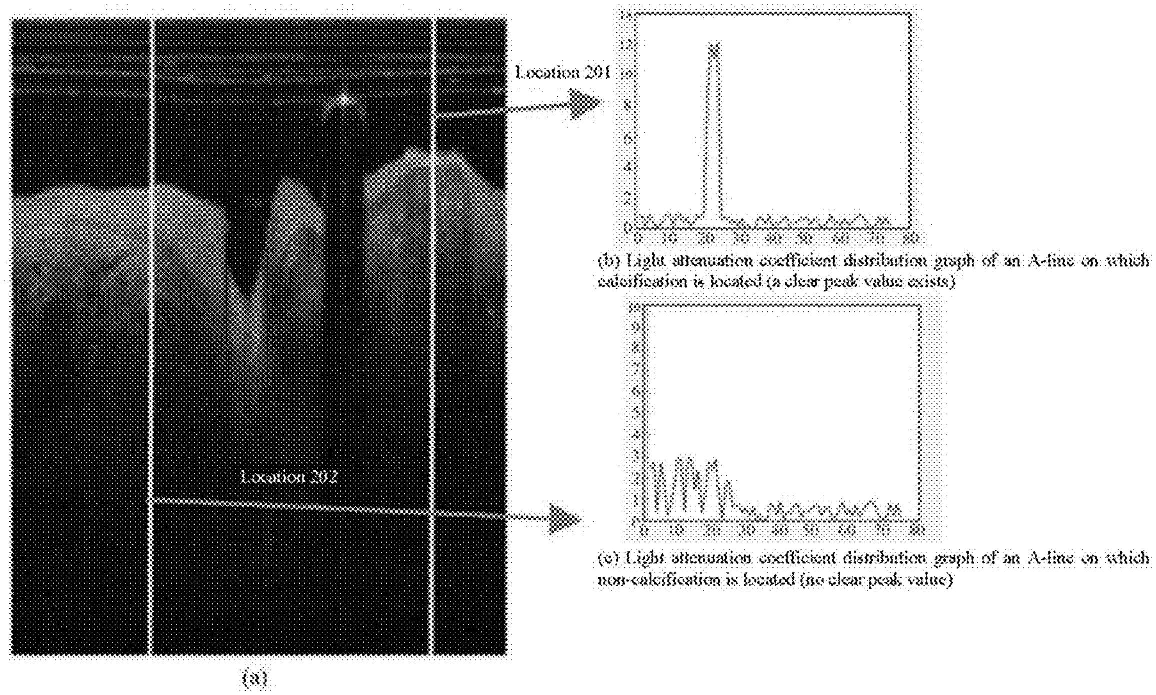
FIG. 2 is a schematic diagram of a light attenuation coefficient distribution of A-lines in a calcified region and a non-calcified region according to an embodiment of the present application.

The above single light attenuation coefficient training image has a total of 500 A-lines (that is, a plurality of A-lines of the blood vessel OCT training image). One light attenuation coefficient distribution curve may be drawn for 642 light attenuation coefficient values (that is, 642 pixels) on each A-line in the 500 A-lines. When the light attenuation coefficient value on the light attenuation coefficient distribution curve presents a trend of being low, suddenly becoming high, and then decreasing, and a light attenuation coefficient value (that is, a peak value) of the highest point on the light attenuation coefficient distribution curve is greater than a given threshold (for example, the given threshold is 8), it indicates that calcification is present on the A line. In addition, a boundary of calcification appears near the peak value. Therefore, the pixel at which the peak value is located is a calcified point of interest. The above given threshold is used for representing that light attenuation coefficient values on the A-line reach a light attenuation coefficient value of a calcified region. As shown in FIG. 2, FIG. (a) is a blood vessel OCT image. A light attenuation coefficient distribution curve of an A-line on which a location 201 is located in FIG. (a) is shown in FIG. (b). FIG. (b) is a diagram of a light attenuation coefficient of an A-line on which calcification is located. The horizontal coordinate represents the $1^{st}$ to $500^{th}$ A-lines. The vertical coordinate represents the light attenuation coefficient value. As can be seen from FIG. (b), a clear peak value exists in an interval [20, 30], and the point peak value is clearly greater than the given threshold (for example, the given threshold is 8). Therefore, calcification is present on the A-line on which the location 201 is located. That is, a pixel on which the location 201 is located is a calcified point of interest. A light attenuation coefficient distribution curve of an A-line on which a location 202 is located in FIG. (a) is shown in FIG. (c). FIG. (c) is a diagram of a light attenuation coefficient of an A-line on which non-calcification is located. A horizontal coordinate represents the $1^{st}$ to $500^{th}$ A-lines. A vertical coordinate represents a light attenuation coefficient value. As can be seen from FIG. (c), there is no clear peak value in an interval [0, 80], and the largest light attenuation coefficient value in the interval [0, 80] is also less than the given threshold (for example, the given threshold is 8). Therefore, no calcification is present on the A-line on which the location 202 is located. That is, a pixel on which the location 202 is located is a non-calcified point of interest.

Figure 3:
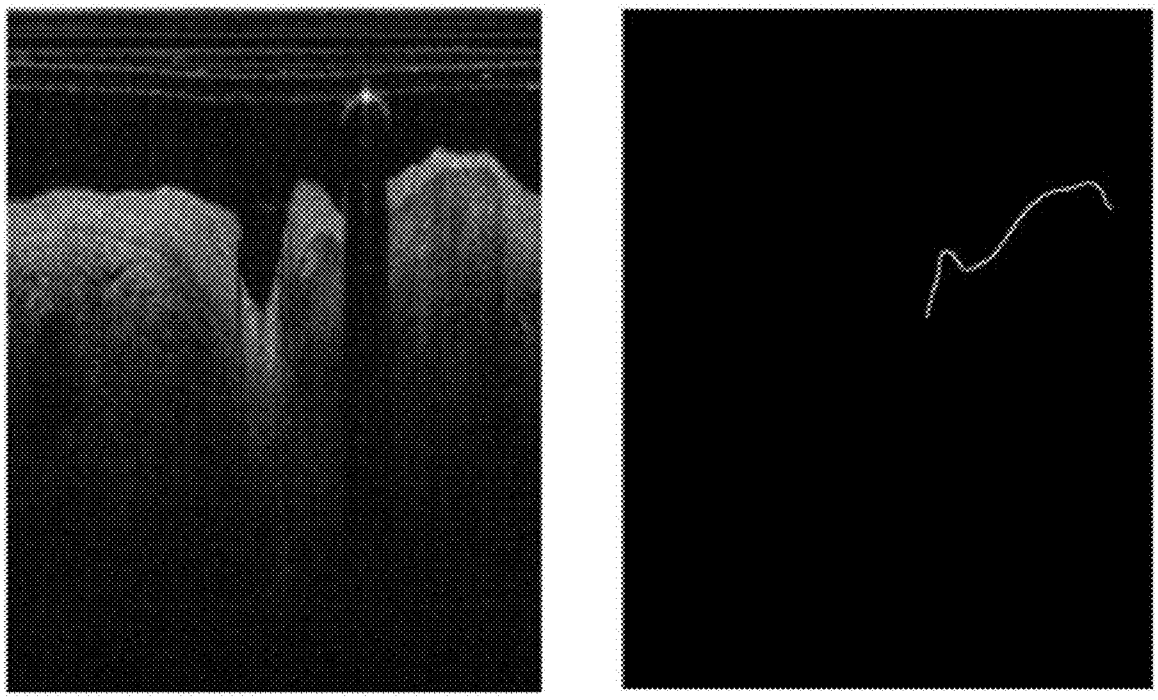
FIG. 3 is a schematic diagram of a calcified region of interest according to an embodiment of the present application.

For example, the region of interest (that is, the calcified region of interest image) of the intravascular OCT training image is determined according to a pixel corresponding to the largest light attenuation coefficient on each A-line in the plurality of A-lines. Intravascular blood vessel tissue is used as an example. A single blood vessel OCT image has 500 A-lines. One calcified point of interest is determined on each A-line. 500 calcified points of interest may be determined from the 500 A-lines. The calcified region of interest image may be obtained by connecting the 500 calcified points of interest, as shown in FIG. 3. (a) is an OCT image (that is, the blood vessel OCT image). (b) shows the calcified region of interest image. In the calcified region of interest image, the white curve is the calcified region of interest. Pixel values on the white curve are 1. Pixel values at locations other than white curve in the calcified region of interest image are 0).

Next, extraction of a texture feature in the blood vessel OCT image using a texture feature extraction algorithm is described.

For example, the step of acquiring a texture feature matrix of a calcified plaque region in the intravascular OCT training image includes: determining a spatial gray-level co-occurrence matrix of the intravascular OCT training image; determining at least one texture feature of the intravascular OCT training image according to the spatial gray-level co-occurrence matrix; and determining the texture feature matrix according to the texture feature. For example, intravascular blood vessel tissue is used as an example. A spatial gray-level co-occurrence matrix (that is, a correlation matrix) of the blood vessel OCT image (that is, the blood vessel OCT training image) is calculated by using a texture feature statistical analysis method. At least one texture feature of the blood vessel OCT training image is further extracted according to the spatial gray-level co-occurrence matrix. The at least one texture feature includes one or more of energy, contrast, entropy, and correlation.

For example, energy of the blood vessel OCT training image, contrast of the OCT training image, entropy of the OCT training image, and correlation of the OCT training image are calculated according to the spatial gray-level co-occurrence matrix. The energy of the blood vessel OCT training image is a square sum of element values of the spatial gray-level co-occurrence matrix, and reflects the uniformity and texture thickness of a gray-level distribution of the blood vessel OCT training image. The contrast of the blood vessel OCT training image reflects image definition and the depth of texture grooves. When the texture grooves are deeper, contrast of the image is larger, and a visual effect is clearer. The entropy of the blood vessel OCT training image is a measurement of an amount of information that the image has, and is used for representing the non-uniformity or complexity of texture in the image. The correlation of the blood vessel OCT training image is a measurement of a similarity between elements of the spatial gray-level co-occurrence matrix in a row or column direction, and is used for reflecting a local gray-level correlation in the image. The texture feature of the blood vessel OCT training image may be extracted in spatial domain, and the texture feature of the blood vessel OCT training image may also be extracted in transform domain by using discrete cosine changes and local Fourier changes. In addition, average pixel intensity (that is, an average value, also called a first-order statistical quantity) calculation and variance (that is, a second-order statistical quantity) calculation may be further performed on the pixels of the blood vessel OCT training image, to represent a texture feature of the blood vessel OCT image.

The texture feature of the blood vessel OCT training image is extracted by using the above method. For each pixel in the blood vessel OCT training image, one multi-dimensional vector, that is, a 1×K multi-dimensional texture feature vector may be obtained. K is a quantity of texture extracted features of the blood vessel OCT training image. For example, when four texture features, for example, the energy of the blood vessel OCT training image, inertia of the blood vessel OCT training image, the entropy of the blood vessel OCT training image, and the correlation of the blood vessel OCT training image are extracted, in this case, a value of K is 4. For a blood vessel OCT training image with an image size of 642×500, the texture feature of the blood vessel OCT training image is extracted by using the texture feature statistical analysis method. Finally, a 642×500×K texture feature matrix (that is, an OCT texture feature matrix) may be obtained. The texture feature matrix is used for assisting in training a convolutional neural network to be trained.

Finally, it is described that using texture features of a region of interest (that is, a calcified region of interest image) and a blood vessel OCT training image to assist in training of a convolutional neural network to be trained to generate a target convolutional neural network and then precisely identifying the calcified plaque region in the blood vessel OCT image by using the target convolutional neural network.

Figure 4:
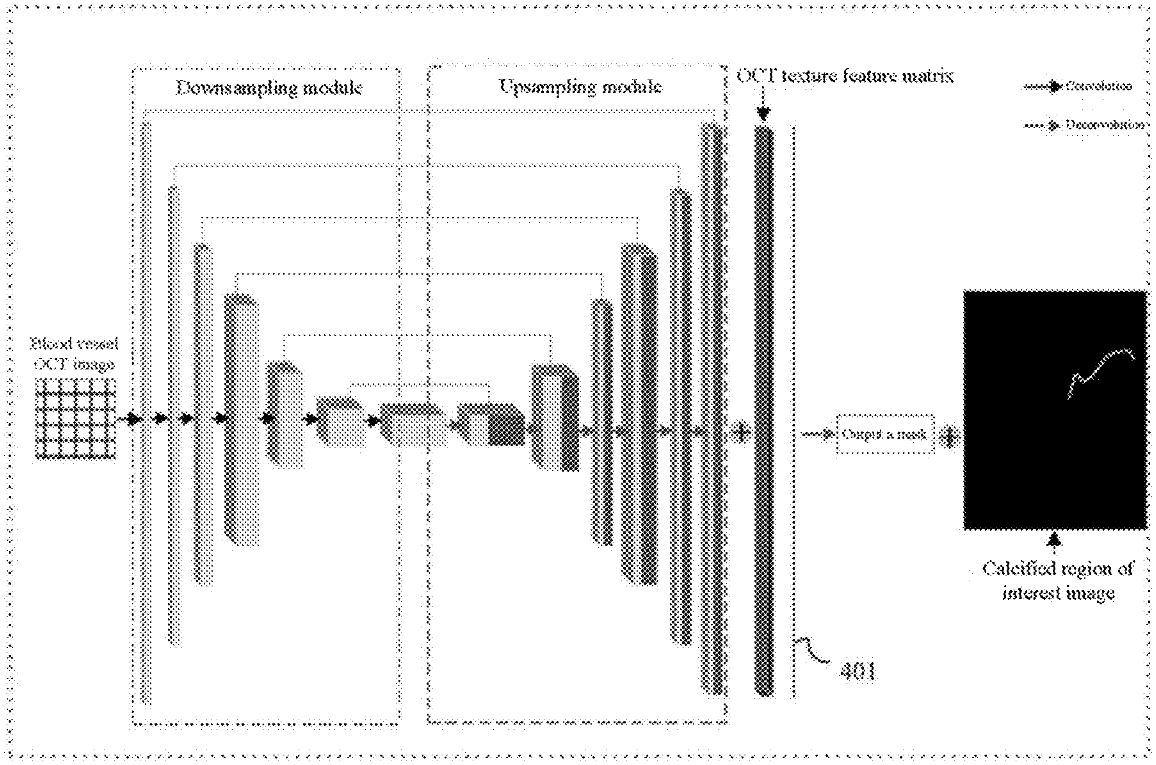
FIG. 4 is a schematic diagram of a network model according to an embodiment of the present application.

For example, the convolutional neural network to be trained is a U-net model. As shown in FIG. 4, the convolutional neural network to be trained has a total of five convolutional modules (that is, downsampling modules) and five deconvolutional modules (that is, upsampling modules). Each module includes three layers of convolution. Each convolution is followed by a pooling layer, a non-linear activation function, and a normalization layer. A convolutional core of each layer of convolution has a size of 3×3. A Relu function is used for an internal non-linear activation function. An average pooling manner is used in the pooling layer. In a process of training the convolutional neural network to be trained, for a learning rate, a dynamic learning rate is used. An initial learning rate is 0.1. If in each training process of the convolutional neural network to be trained, a loss function of the convolutional neural network to be trained is not clearly reduced, the learning rate is decreased 10 times (that is, 0.01). The reason lies in that, if the loss function remains unchanged when the learning rate has a value, it indicates that a parameter of the convolutional neural network to be trained may oscillate near a value. In this case, it may be further observed, by adjusting the learning rate (for example, by decreasing the learning rate, to slightly reduce a learning speed of the convolutional neural network to be trained), whether the loss function of the convolutional neural network to be trained is decreased. If the loss function is not decreased, it indicates that the convolutional neural network to be trained is already an optimal network. If the loss function is decreased, it indicates that the convolutional neural network to be trained further needs more training. For example, the foregoing training dataset is used. The training dataset includes 15000 blood vessel OCT training images. The convolutional neural network to be trained is trained 80 times (that is, epoch is set to 80, where epoch represents a quantity of times of cyclic training of the training dataset). Training is completed once the convolutional neural network to be trained has trained the 15000 blood vessel OCT images. In the above 15000 blood vessel OCT training images, every eight blood vessel OCT training images inputted as a set (that is, a batch size is set to 8) into the convolutional neural network to be trained to perform training. A current time of training ends when all the 15000 blood vessel OCT training images have been trained.

For example, the intravascular OCT image is processed by using a target convolutional neural network to determine the calcified plaque region of the intravascular OCT image. For example, intravascular blood vessel tissue is used as an example. Any blood vessel OCT image is inputted into a trained target neural network (for example, a trained U-net model). The target neural network outputs the calcified plaque region in the blood vessel OCT image after processing the blood vessel OCT image.

For example, the foregoing target convolutional neural network may be obtained through training by using the following method: processing an intravascular OCT training image by using a convolutional neural network to be trained to generate a first feature map; acquiring a texture feature matrix of a calcified plaque region in the intravascular OCT training image; generating a predicted mask according to the first feature map and the texture feature matrix; acquiring a region of interest of the intravascular OCT training image, where the region of interest is used for representing a calcified plaque region in the intravascular OCT training image; and training the convolutional neural network to be trained according to the predicted mask, the region of interest, and a standard mask to generate the target convolutional neural network, where the predicted mask is a predicted value, the standard mask is an actual value, and the region of interest is used for optimizing a loss function of the convolutional neural network to be trained.

For example, intravascular blood vessel tissue is used as an example. The convolutional neural network to be trained is a U-net model. As shown in FIG. 4, a set of blood vessel OCT training images are inputted into the U-net model. A size of each blood vessel OCT training image is 642×500. A process of processing the blood vessel OCT training image by the U-net model is as follows: First, the blood vessel OCT training image with a size of 642×500 is inputted into the downsampling modules. Specifically, the blood vessel OCT training image undergoes convolutional processing by the first convolutional module to output image data with a size of 320×250×32. 32 is a quantity of channels. Subsequently, image data of 32 channels sequentially undergoes convolutional processing to obtain image data of 64 channels, image data of 128 channels, image data of 256 channels, image data of 512 channels, and image data of 1024 channels. An image size of the 1024 channels is 20×16×1024. Subsequently, image data of the 1024 channels with an image size of 20×16 is inputted into the upsampling modules. The image data with the image size of 20×16 undergoes deconvolutional processing by the first upsampling module to output image data of 40×30×512. 512 is a quantity of channels. Subsequently, the image data of 512 channels sequentially undergoes deconvolutional processing to obtain image data of 256 channels, image data of 128 channels, image data of 64 channels, and image data of 32 channels. Image data of 32 channels with an image size of 642×500 (that is, image data of 642×500×32). The image data of 642×500 (that is, the first feature map) is image data outputted by the last upsampling module.

For example, the step of generating a predicted mask according to the first feature map and the texture feature matrix (that is, the texture feature matrix of the blood vessel OCT training image) includes: splicing the first feature map and the texture feature matrix to generate a second feature map; and performing dimensionality reduction on the second feature map to generate the predicted mask. The above texture feature matrix of the blood vessel OCT training image is a texture feature matrix obtained by extracting a texture feature of a calcified plaque region in the blood vessel OCT training image by using texture feature statistical analysis method. Specifically, because the above texture feature matrix of the K-dimensional blood vessel OCT training image has a size of 642×500, which is the same as an image size of 32 channels (that is, 642×500) outputted by a U-net neural network. To effectively use the texture feature matrix of the blood vessel OCT training image, the matrix (that is, the first feature map) of 642×500×32 outputted by the last upsampling module is spliced with the OCT texture feature matrix (that is, the texture feature matrix of the blood vessel OCT training image), as shown in FIG. 4, to obtain one second feature map 401. For the second feature map 401, dimensionality reduction is performed on the second feature map by using three 1×1 convolutional layers. The second feature map 401 is processed by the first 1×1 convolutional layer to output a third feature map of 642×500×16. The third feature map is processed by the second 1×1 convolutional layer to output a fourth feature map of 642×500×8. The fourth feature map is processed by the third 1×1 convolutional layer to output a fifth feature map of 642×500. The fifth feature map corresponds to an outputted mask (that is, the prediction mask) in FIG. 4.

For example, the above convolutional neural network to be trained is trained according to the above predicted mask, the region of interest, and the standard mask, to generate the target convolutional neural network. A loss function (that is, a Loss function) of a U-net model is constructed according to a calcified region of interest and a non-calcified region in a calcified region of interest image shown FIG. 2(*b*). The Loss function is as follows:

$$\text{Loss} = |P_{mask} - G_{mask}| \cdot * (\omega * M_{ROI} + \varepsilon)$$

wherein, $P_{mask}$ represents a predicted calcified mask (that is, the prediction mask). The prediction mask is the predicted value. $G_{mask}$ represents a gold standard calcified mask (that is, the standard mask). The standard mask is the actual value. $M_{ROI}$ represents the calcified region of interest image (that is, a region of interest). ω represents a weight coefficient of the region of interest, and usually ω>1. ε is a weight coefficient of a background region (a non-calcified region), and usually 0<ε<1. The above gold standard calcified mask is a calcified mask generated by performing binary processing on the foregoing blood vessel OCT training image with a calcified plaque region already annotated by the medical specialists. The calcified mask is a binary image of 0s and 1s. 0 represents a non-calcified plaque region, and 1 represents a calcified plaque region annotated by the specialists. As can be seen from the above Loss function, the Loss function includes two items. The first item is a loss function of a calcified region of interest: $\text{Loss}=|P_{mask}-G_{mask}|\cdot*(\omega*M_{ROI})$. The second item is a loss function for a region that is a not calcified region of interest: $\text{Loss}=|P_{mask}-G_{mask}|\cdot*\varepsilon$. The first loss function is emphatically optimized in a process of training the U-net model. The reason lies in that, a weight coefficient of the first loss function is larger (for example, ω>1). Therefore, a size of the first loss function determines a change trend of the entire Loss function. For example, when the first loss function has a decreasing trend, the Loss function also has a decreasing trend. A network parameter of the convolutional neural network to be trained keeps being adjusted according to the Loss function. It can indicate only when the Loss function reaches the preset value that the convolutional neural network to be trained has been trained into the target convolutional neural network. In the process of training the convolutional neural network to be trained, the calcified region of interest image may be used for improving a learning capability of a loss function of the convolutional neural network to be trained for edge structure information of the calcified plaque region. In addition, the identification precision of the edge structure information of the calcified plaque region is increased by increasing a weight of the region of interest in the loss function (that is, the first loss function).

Figure 5:
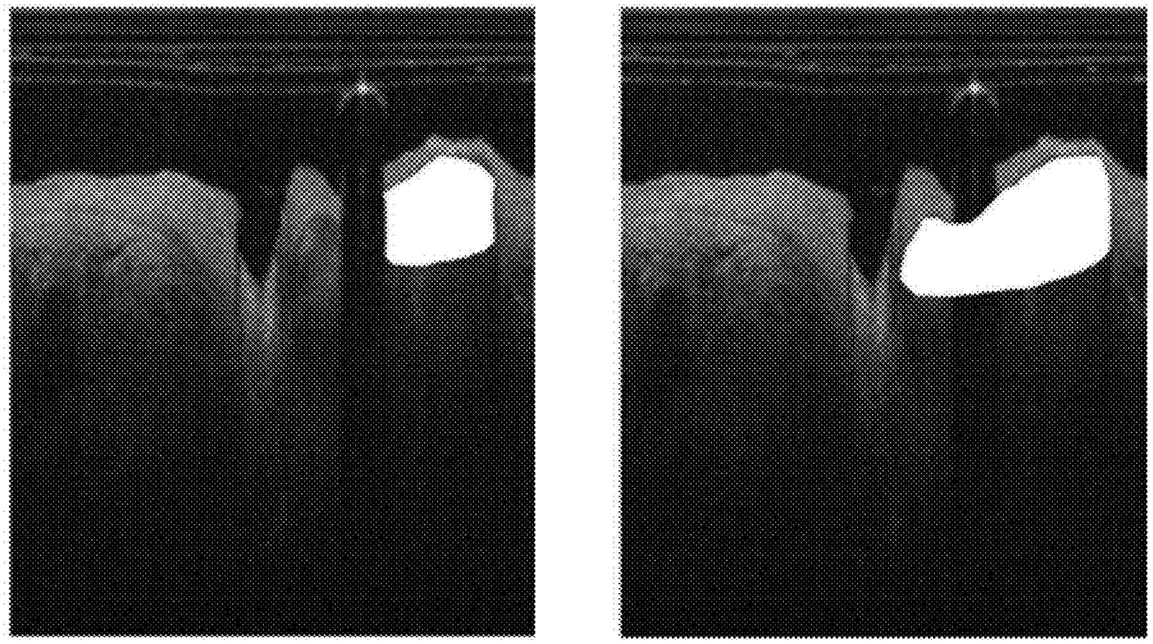
FIG. 5 is a schematic diagram of calcified identification according to an embodiment of the present application.

For example, as shown in FIG. 5, FIG. (a) shows only a result of identifying a calcified plaque region by using a deep learning model without using features in other aspects. FIG. (b) shows a result of identifying a calcified plaque region by using the above technical solution provided in this application. As can be seen FIG. (a) and FIG. (b), a range of calcified plaque regions that can be identified by using the technical solution provided in this application is larger than a range of calcified plaque regions identified by using only a deep learning model. It indicates that the technical solution provided in this application can identify a partial calcified plaque region that cannot be identified by using only a deep learning model. Therefore, the accuracy of identifying a calcified plaque region by using the technical solution provided in this application is higher.

S103: Determine a light attenuation coefficient of the intravascular OCT image, where the light attenuation coefficient of the intravascular OCT image does not include a light attenuation coefficient of the calcified plaque region.

For example, the calcified plaque region in the intravascular OCT image is determined by using the above target convolutional neural network, and a light attenuation coefficient of the calcified plaque region is set to 0, so that a light attenuation coefficient image after calcification is removed can be obtained. Certainly, a calcified plaque region may be determined in a manner of annotation by medical specialists by using professional software, or a calcified plaque region may be determined by using a neural network model. A manner of determining a calcified plaque region in an intravascular OCT image is not limited in this application.

For example, intravascular blood vessel tissue is used as an example. A blood vessel OCT image captured by the OCT device is a blood vessel OCT image in a polar coordinate system. A size of the blood vessel OCT image is 642×500. Therefore, a light attenuation coefficient of each pixel of a blood vessel OCT image may be calculated by using a light attenuation model in the polar coordinate system. A value of the light attenuation coefficient corresponding to each pixel is used to replace a value of each pixel in the blood vessel OCT image, to obtain a light attenuation coefficient training image corresponding to a blood vessel OCT image in the polar coordinate system. A size of the light attenuation coefficient training image is 642×500.

The calcified plaque region in the blood vessel OCT image is identified by using the above target convolutional neural network, and a pixel value (that is, the value of the light attenuation coefficient) of the calcified plaque region in the light attenuation coefficient training image corresponding to the blood vessel OCT image is set to 0, so that a light attenuation coefficient image after a calcified plaque region is removed is obtained. A single light attenuation coefficient image has a total of 500 A-lines. Each A-line has 642 light attenuation coefficient values. The largest light attenuation coefficient value on each A-line is calculated. 500 A-lines have a total of 500 largest light attenuation coefficient values. The 500 largest light attenuation coefficient values form one 1×500 largest light attenuation coefficient vector. That is, for a single light attenuation coefficient image, one 1×500 largest light attenuation coefficient vector may be obtained. If a set of OCT pullback data contains 300 temporally adjacent blood vessel OCT images, 300 light attenuation coefficient images are obtained, and 300 1×500 largest light attenuation coefficient vectors are obtained. The 300 1×500 largest light attenuation coefficient vectors form one 300×500 largest light attenuation coefficient matrix.

For example, an IPA is a statistical ratio of light attenuation coefficient values being greater than a threshold x. The light attenuation coefficient represents a degree of attenuation of light by different tissue in an imaging process. As can be seen from the above analysis, each row of data in the largest light attenuation coefficient matrix is one 1×500 largest light attenuation coefficient vector (that is, each row of data represents one light attenuation coefficient image). The largest light attenuation coefficient vector has a total of 500 elements (that is, 500 largest light attenuation coefficient values $\mu_t$). An IPA value of one (single) light attenuation coefficient image, may be calculated by using the following formula:

$$IPA = \frac{N(\mu_t > x)}{N_{total}} \times 1000 \quad (4)$$

wherein, $N(\mu_t > \chi)$ represents comparing the 500 elements with the threshold x. A quantity of elements being greater than the threshold x in the 500 elements is counted. $N_{total}$ represents a total quantity of A-lines in the light attenuation coefficient image. As can be seen according to the foregoing analysis, 500 largest light attenuation coefficient values $\mu_t$ represents 500 A-lines. Therefore, a value of $N_{total}$ is 500. For example, when $N(\mu_t > \chi)$ is 400, the value of $N_{total}$ is 500, and IPA is 800.

Figure 6:
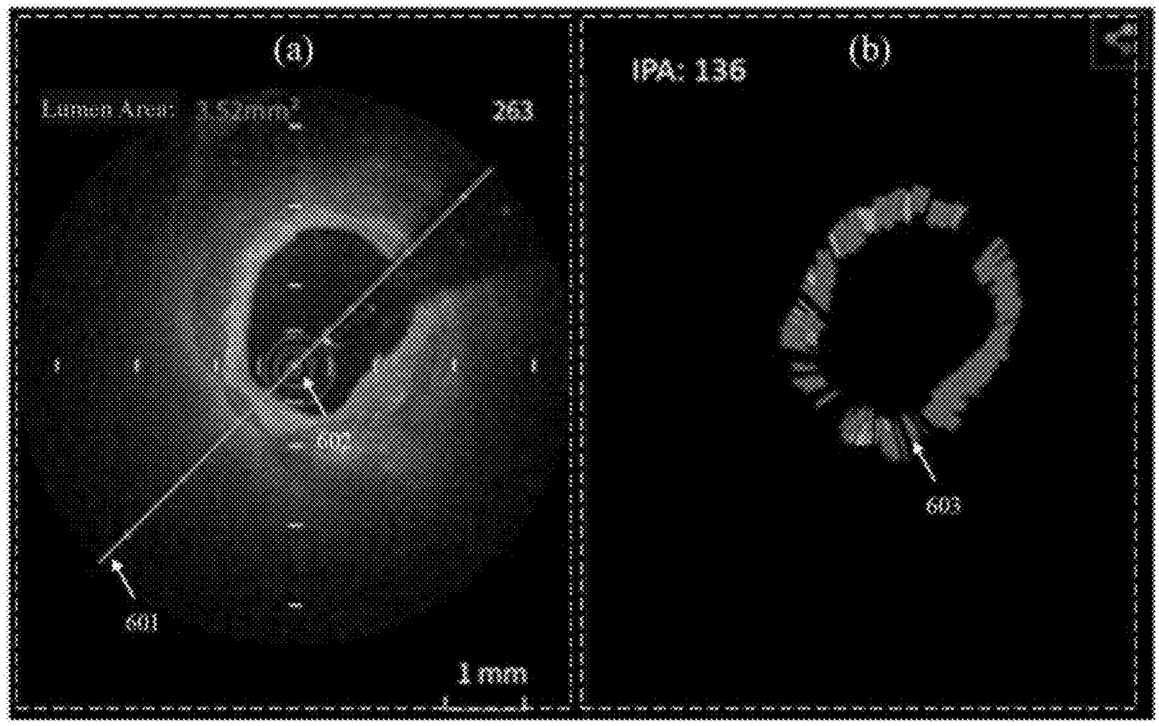
FIG. 6 is a schematic diagram of a light attenuation coefficient image and an IPA value before calcification is removed according to an embodiment of the present application.

For example, because a single blood vessel OCT image acquired by the OCT device has a size of 642×500 (that is, a blood vessel OCT image bar chart). As shown in FIG. 6(*a*). 601 represents an indication line, and 602 represents a calibration cursor. 500 refers to that a total of 500 A-lines are obtained when a catheter performs a 360° pullback in a blood vessel, and 642 refers to that 642 pixels are obtained on each A-line. A light attenuation coefficient of each pixel of the single blood vessel OCT image is calculated by using the light attenuation model to obtain a single light attenuation coefficient image corresponding to the blood vessel OCT image. The single light attenuation coefficient image also has a size of 642×500 (that is, the light attenuation coefficient image bar chart). 500 refers to that a total of 500 A-lines are obtained when a catheter performs a 360° pullback in a blood vessel, and 642 refers to that 642 pixels are obtained on each A-line. The blood vessel OCT image bar chart is converted into a blood vessel OCT image pie chart. Specifically, because a total of 500 A-lines are obtained when the catheter performs the 360° pullback in the blood vessel, one A-line is scanned every 0.72° (that is, 360° divided by 500 equals) 0.72°. In this case, the 500 A-lines are arranged at equal intervals of 0.72° to form a circle to obtain the blood vessel OCT image pie chart. A method for converting a light attenuation coefficient image bar chart into a light attenuation coefficient image pie chart is the same as a method for converting a blood vessel OCT image bar chart into a blood vessel OCT image pie chart. Details are not described herein again. The light attenuation coefficient image pie chart is shown in FIG. 6(*b*). 603 represents a vascular wall.

To better display a blood vessel OCT image pie chart and a corresponding light attenuation coefficient image pie chart on a software interface to facilitate observation, linear interpolation is performed on each pixel in the blood vessel OCT image pie chart by using a bilinear interpolation algorithm. Specifically, linear interpolation is performed on the blood vessel OCT image pie chart in an x direction and a y direction by using four surrounding adjacent domain pixels, to obtain a blood vessel OCT image pie chart after interpolation. A method for performing linear interpolation on a light attenuation coefficient image pie chart corresponding to the blood vessel OCT image pie chart is similar to the method for performing linear interpolation on the blood vessel OCT image pie chart. Details are not described herein again. The blood vessel OCT image pie chart obtained by performing linear interpolation and the corresponding light attenuation coefficient image pie chart after interpolation are shown in FIG. 6(*b*) and FIG. 7(*b*) respectively.

For example, as shown in FIG. 6, when the calcified plaque region in the blood vessel OCT image is not removed, an IPA value is directly calculated according to the light attenuation coefficient image corresponding to the blood vessel OCT image. In this case, the IPA value (that is, IPA=136) is very high. Due to the presence of a calcified plaque region, the light attenuation coefficient of the calcified plaque region in the blood vessel OCT image is very high, leading to a slightly high calculation result of IPA. In this case, the IPA calculation result cannot indicate that the blood vessel contains TCFA. Therefore, the calcified plaque region in the blood vessel OCT image needs to be removed before an IPA value can be accurately calculated.

S104: Determine an IPA of the intravascular OCT image according to the light attenuation coefficient of the intravascular OCT image.

Figure 7:
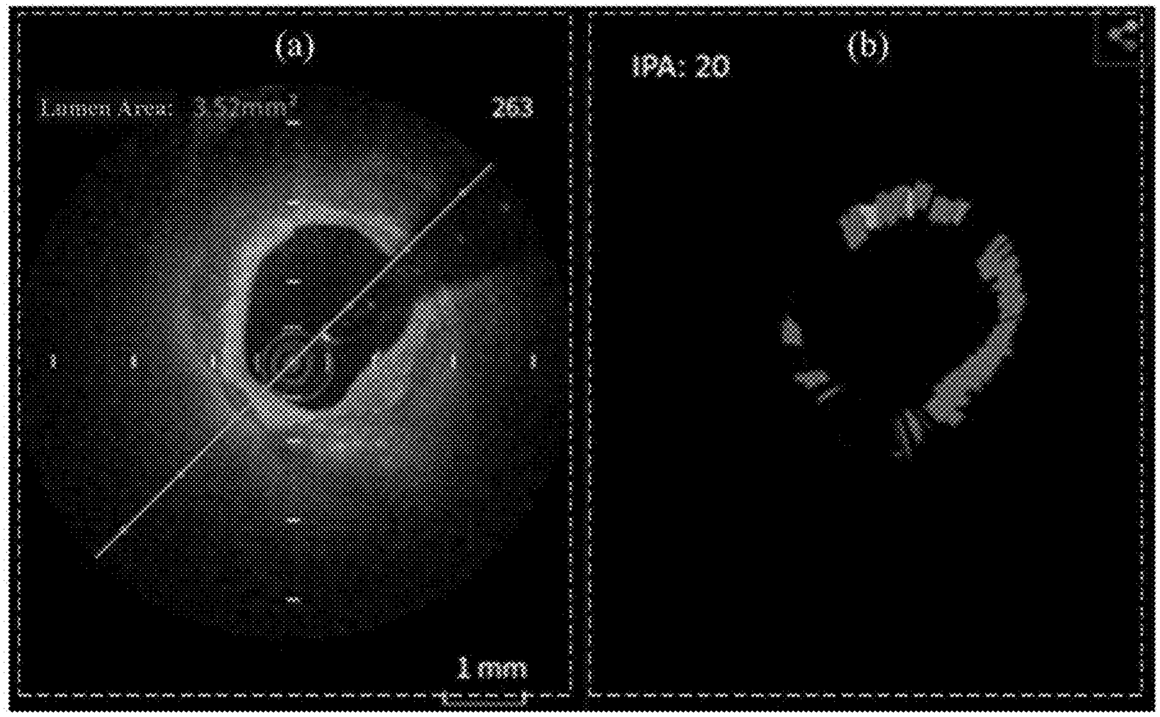
FIG. 7 is a schematic diagram of a light attenuation coefficient image and an IPA value after calcification is removed according to an embodiment of the present application.

For example, intravascular blood vessel tissue is used as an example. As shown in FIG. 7, the calcified plaque region in the blood vessel OCT image is identified by using the above target convolutional neural network, and then a pixel value of the calcified plaque region in the blood vessel OCT image is set to 0. A pixel value (that is, the value of the light attenuation coefficient) of the corresponding calcified plaque region in the light attenuation coefficient training image is 0, so that a light attenuation coefficient image after a calcified plaque region is removed is obtained. The IPA value of the light attenuation coefficient image after the calcified plaque region is removed is calculated, and it is found that the IPA value of the light attenuation coefficient image (that is, IPA=20) is very low. As can be seen, it is found by comparing an IPA value corresponding to a light attenuation coefficient image (FIG. 6(*b*)) before the calcified plaque region in the blood vessel OCT image is removed (FIG. 6(*b*)) and an IPA value corresponding to the light attenuation coefficient image (FIG. 7(*b*)) after the calcified plaque region is removed that the IPA value corresponding to the light attenuation coefficient image after the calcified plaque region is removed is lower. The reason lies in that, the light attenuation coefficient of the calcified region in the light attenuation coefficient image after the calcified plaque region is removed is lower, and there is no impact of the calcified plaque region in the blood vessel OCT image on the IPA calculation result, so that accuracy of TCFA identification using IPA is increased.

Figure 8:
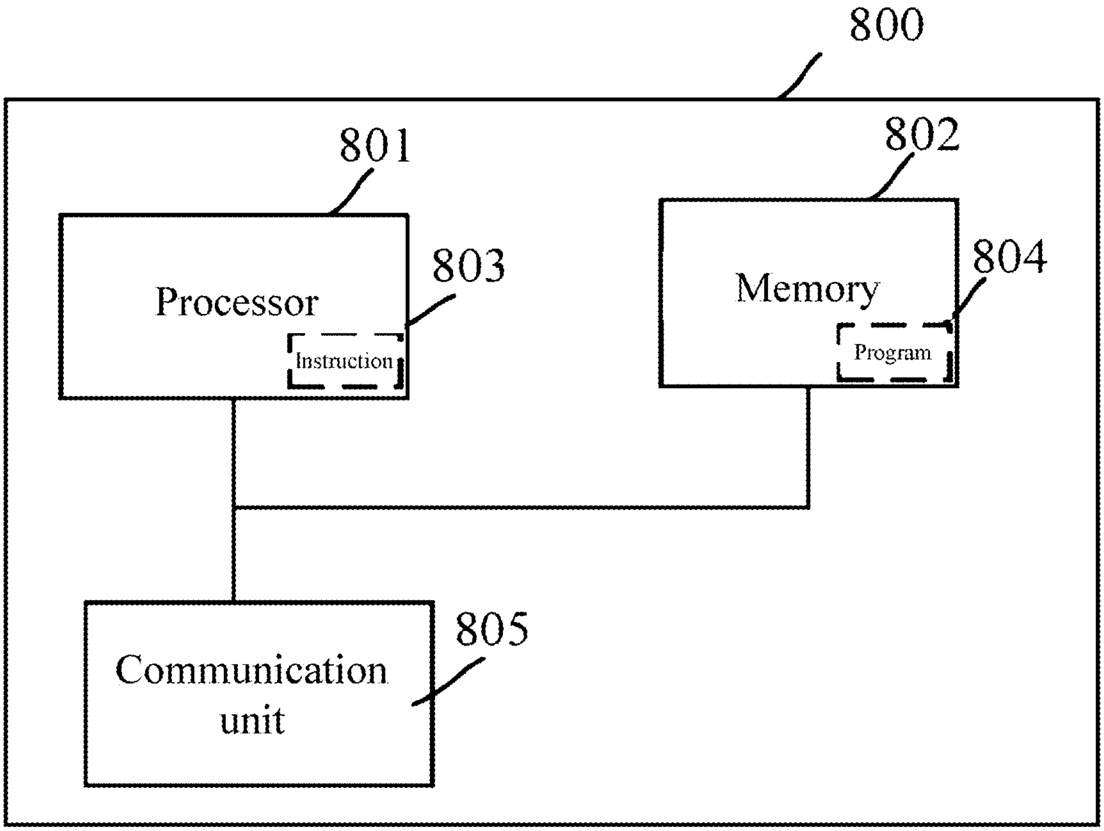
FIG. 8 is a structure diagram of a device for calculating an IPA of an intravascular OCT image according to an embodiment of the present application.

FIG. 8 is a schematic structural diagram of a device for calculating an IPA of an intravascular OCT image according to this application. A dash line in FIG. 8 represents that the unit or the module is optional. A device 800 may be configured to implement the method described in the above method embodiments. The device 800 may be a terminal device or a server or a chip.

The device 800 includes one or more processors 801. The one or more processors 801 may support implementation of the method in the method embodiment corresponding to FIG. 1 by the device 800. The processor 801 may be a general-purpose processor, a dedicated processor. For example, the processor 801 may be a central processing unit (CPU). The CPU may be configured to control the apparatus 800, execute a software program, and/or process data in the software program. The device 800 may further include a communication unit 805, configured to implement input (reception) and output (transmission) of signals.

For example, the device 800 may be a chip. The communication unit 805 may be an input and/or output circuit of the chip. Alternatively, the communication unit 805 may be a communication interface of the chip. The chip may be used as a component of the terminal device.

In another example, the device 800 may be a terminal device. The communication unit 805 may be a transceiver of the terminal device. Alternatively, the communication unit 805 may be a transceiver circuit of the terminal device.

The device 800 may include one or more memories 802, storing a program 804. The program 804 may be executed by the processor 801, to generate an instruction 803, to enable the processor 801 to perform, according to the instruction 803, the method described in the above method embodiments. Optionally, the memory 802 may further store data (for example, an ID of a to-be-tested chip). Optionally, the processor 801 may further read data stored in the memory 802. The data may be stored at the same storage address as the program 804, or the data may be stored at different storage addresses of the program 804.

The processor 801 and the memory 802 may be separately disposed, or may be integrated together, for example, integrated on a system on chip (SOC) of the terminal device.

For a specific manner in which the processor 801 performs the method for calculating an IPA of an intravascular OCT image, refer to related descriptions in the method embodiments.

It should be understood that, the steps in the foregoing method embodiments may be accomplished logic circuits in a hardware form or instructions in a software form in the processor 801. The processor 801 may be a CPU, a digital signal processor (DSP), a field-programmable gate array (FPGA) or another programmable logic device, for example, a discrete gate, a transistor logic device, or a discrete hardware component.

This application further provides a computer program product. When the computer program product is executed by the processor 801, the method in any method embodiment in this application is implemented.

The computer program product may be stored in the memory 802, and is, for example, the program 804. The program 804 is ultimately converted into an executable target file capable of being executed by the processor 801 after going through a process of preprocessing, compiling, assembling, and linking.

This application further provides a computer-readable storage medium, storing a computer program. When the computer program is executed by a computer, the method in any method embodiment of this application is implemented. The computer program may be a high-level language program, or may be an executable target program.

The non-transient computer-readable storage medium is, for example, the memory 802. The memory 802 may be a volatile memory or a non-volatile memory. Alternatively, the memory 802 may include both a volatile memory and a non-volatile memory. The non-volatile memory may be a read-only memory (ROM), a programmable ROM (PROM), an erasable PROM (EPROM), an electrically EPROM (EEPROM), or a flash memory. The volatile memory may be a random access memory (random access memory, RAM), used as an external cache. By way of example rather than limitation, many forms of RAMs such as a static RAM (SRAM), a dynamic RAM (DRAM), a synchronous DRAM (SDRAM), a double-data-rate (DDR) SDRAM, an enhanced SDRAM (ESDRAM), a synchronous-link DRAM (synchlink DRAM or SLDRAM), and a direct rambus RAM (DRRAM) may be used.

It may be clearly understood by a person skilled in the art that, for the purpose of convenient and brief description, for a detailed working process of the foregoing apparatuses and devices and generated technical effects, refer to a corresponding process and technical effects in the foregoing method embodiments, and details are not described herein again.

In several embodiments provided in this application, the disclosed system, apparatus, and method may be implemented in another manner. For example, some features in the method embodiments described above may be ignored or not performed. The described apparatus embodiments are merely examples. Division into the units is merely logical function division and may be other division during actual implementation. A plurality of units or components may be combined or integrated into another system. In addition, the coupling between the units or the coupling between the components may be direct coupling or indirect coupling. The coupling includes electrical, mechanical or other forms of connection.

The embodiments are merely intended for describing the technical solutions of this application other than limiting this application. Although this application is described in detail with reference to the foregoing embodiments, persons of ordinary skill in the art should understand that they may still make modifications to the technical solutions described in the foregoing embodiments or make equivalent replacements to some technical features thereof, without departing from the spirit and scope of the technical solutions of embodiments of this application, and shall all fall within the scope of protection of this application.

What is claimed is:

1. A method for calculating an index of plaque attenuation (IPA) of an intravascular optical coherence tomography (OCT) image, wherein the method comprises:

acquiring an intravascular OCT image by scanning intravascular blood vessels through an OCT device;

determining a calcified plaque region of the intravascular OCT image by using a target convolutional neural network;

determining an attenuation coefficient of the intravascular OCT image by using the target convolutional neural network, wherein the attenuation coefficient of the intravascular OCT image does not comprise an attenuation coefficient of the calcified plaque region; and determining an IPA of the intravascular OCT image according to the attenuation coefficient of the intravascular OCT image;

wherein the step of determining a calcified plaque region of the intravascular OCT image comprises:

processing the intravascular OCT image by using the target convolutional neural network to determine the calcified plaque region of the intravascular OCT image;

wherein the target convolutional neural network is obtained through training by using the following method:

processing an intravascular OCT training image by using a convolutional neural network to be trained to generate a first feature map;

acquiring a texture feature matrix of a calcified plaque region in the intravascular OCT training image;

generating a predicted mask according to the first feature map and the texture feature matrix;

acquiring a region of interest of the intravascular OCT training image, wherein the region of interest is used for representing a calcified plaque region in the intravascular OCT training image; and training the convolutional neural network to be trained according to the predicted mask, the region of interest, and a standard mask to generate the target convolutional neural network, wherein the predicted mask is a predicted value, the standard mask is an actual value, and the region of interest is used for improving a learning capability of a loss function of the convolutional neural network to be trained for edge structure information of the calcified plaque region.

2. The method according to claim 1, wherein the step of acquiring a region of interest of the intravascular OCT training image comprises:

acquiring a plurality of A-lines of the intravascular OCT training image; and determining the region of interest of the intravascular OCT training image according to a pixel corresponding to the largest attenuation coefficient on each A-line in the plurality of A-lines.

3. The method according to claim 1, wherein the step of generating a predicted mask according to the first feature map and the texture feature matrix comprises:

splicing the first feature map and the texture feature matrix to generate a second feature map; and performing dimensionality reduction on the second feature map to generate the predicted mask.

4. The method according to claim 3, wherein the step of performing dimensionality reduction on the second feature map comprises:

performing the dimensionality reduction on the second feature map by using three 1×1 convolutional layers.

5. The method according to claim 1, wherein the step of acquiring a texture feature matrix of a calcified plaque region in the intravascular OCT training image comprises:

determining a spatial gray-level co-occurrence matrix of the intravascular OCT training image;

determining at least one texture feature of the intravascular OCT training image according to the spatial gray-level co-occurrence matrix; and determining the texture feature matrix according to the texture feature.

6. The method according to claim 5, wherein the at least one texture feature comprises:

one or more of energy, inertia, entropy, and correlation.

7. A device for calculating an IPA of an intravascular OCT image, wherein the device comprises a processor and a memory, the memory is configured to store a computer program, and the processor is configured to call the computer program from the memory and run the computer program, to enable the device to implement the method according to claim 1.

8. A non-transitory computer-readable storage medium, wherein the non-transitory computer-readable storage medium stores a computer program, and the computer program, when executed by a processor, enables the processor to implement the method according to claim 1.

* * * * *